US00PP12333P2

(12) United States Plant Patent
Heims

(10) Patent No.: US PP12,333 P2
(45) Date of Patent: Jan. 8, 2002

(54) PULMONARIA PLANT NAMED 'DARK VADER'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/628,783

(22) Filed: Jul. 31, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Pulmonaria plant characterized by a unique combination of dark, thick leaves with good silver spotting and compact habit.

1 Drawing Sheet

The present invention relates to a new and distinct hybrid of Pulmonaria, of the family Boraginaceae, which originated as a cross between a patented Pulmonaria 'Victorian Brooch' U.S. Plant Pat. No. 11,234 (seed parent) and an unknown pollen parent. This is known to be an outcross because Pulmonaria does not normally self-pollinate. As the instant plant and its parent plants are of hybrid origin, no species designation is assigned.

This new Pulmonaria is the result of a controlled cross of the aforementioned plants at Terra Nova Nurseries, Inc., in Canby, Oreg. This hybrid was selected from a large selection of seedlings. Seed parent plants were retained to observe habit and to compare with the instant plant. The new variety has been reproduced only by asexual propagation (division and tissue culture). Each of the progeny exhibits identical characteristics to the original plant.

This plant is characterized by the following:

1. Dark, thick leaves with good silver spotting.
2. Compact, round habit when in bloom.

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows Pulmonaria 'Dark Vader' in Portland, Oreg.

DETAILED PLANT DESCRIPTION

The following is a detailed description of the new Pulmonaria hybrid based on observations of one and a half year old specimens grown in the field in Canby, Oreg. The color descriptions are all based on The *Royal Horticultural Society Colour Chart.*

Plant:
- *Type.*—Herbaceous perennial.
- *Hardiness.*—USDA Zones 4 to 9.
- *Size.*—56 to 64 cm wide and 31 to 35 cm tall.
- *Form.*—Basal clump.

Foliage:
- *Type.*—Simple.
- *Shape.*—Lanceolate.
- *Length.*—15 to 20 cm.
- *Width.*—8 to 11 cm.
- *Petiole length.*—11.5 to 14.5 cm.
- *Margins.*—Entire-ciliate.
- *Apex.*—Narrowly-acute.
- *Base.*—Attenuate.
- *Leaf texture.*—Setose.
- *Petiole texture.*—Setulose.
- *Leaf arrangement.*—Rosette.
- *Venation.*—Reticulate.

Flower bud:
- *Size.*—1 cm deep and 0.4 cm wide.
- *Description.*—Ovoid shape, about 0.4 cm exposed from calyx.

Flower:
- *Type.*—Perfect.
- *Shape.*—Funnelform.
- *Size.*—1–1.2 mm from petal tip to petal tip.
- *Corolla.*—5 fused petals with rounded lobes.
- *Calyx.*—5 fused sepals, lobes acute, cut in top ⅓ of calyx.
- *Calyx size.*—1.5 cm deep and 0.6 cm wide.
- *Calyx shape.*—Campanulate.
- *Calyx texture.*—Hispid and glandular hairy.
- *Pistil.*—Thrum type, included in the corolla tube.
- *Ovary position.*—Partly inferior.
- *Carpel number.*—4.
- *Stamen number.*—5, exerted from the corolla tube.
- *Inflorescence type.*—Forked cymes.
- *Flower number per inflorescence.*—20–30.
- *Peduncle width.*—3 mm tapering to 1 mm.
- *Peduncle texture.*—Setose.
- *Blooming height.*—14–16 cm.
- *Bloom period.*—Late February to late April.
- *Fragrance.*—None.

Fruit:
- *Type.*—4 smooth nutlets.
- *Fertility.*—Sterile, no noticeable seed produced.

Disease: None observed on plant grown commercially in Canby, Oreg.

Color Characteristics

Foliage:

*Upper surface.*—RHS 136A Green Group.

*Upper surface, spots.*—RHS 190A–B Greyed-Green Group.

*Lower surface.*—RHS 191A Greyed-Green Group.

Flower:

*Bud.*—RHS 53B Red Group.

*Petals.*—RHS 48A Red Group fading to RHS 51C Red Group then turning to RHS 76A Purple Group and senescing to RHS 96A Violet-Blue Group before wilting.

*Calyx.*—RHS 146D Yellow-Green Group.

*Pollen.*—RHS 155A White Group.

Peduncle: RHS 144A–B Yellow-Green Group.

DESCRIPTION OF PARENT PLANTS

The instant plant resulted from a cross between a patented Pulmonaria 'Victorian Brooch'(seed parent) and an unknown pollen parent. Pulmonaria 'Victorian Brooch', as described in U.S. Plant Pat. No. 11,234, has very large flowers on a compact scape and distinctive spotted, ovate foliage. The instant plant differs from Pulmonaria 'Victorian Brooch' in having different colored flowers as well as a different leaf and spotting pattern.

Compared to Pulmonaria 'High Contrast' (U.S. Plant Patent application Ser. No. 09/628,782), the instant plant has less silver in its leaves, a thrum type pistil (included in the corolla tube) rather than a pin type (exerted from the pollen tube), and a round habit rather than a low habit and is taller when in flower.

I claim:

1. A new and distinct hybrid of Pulmonaria plant substantially as shown and described, characterized by a unique combination of dark, thick leaves with good silver spotting and compact habit.

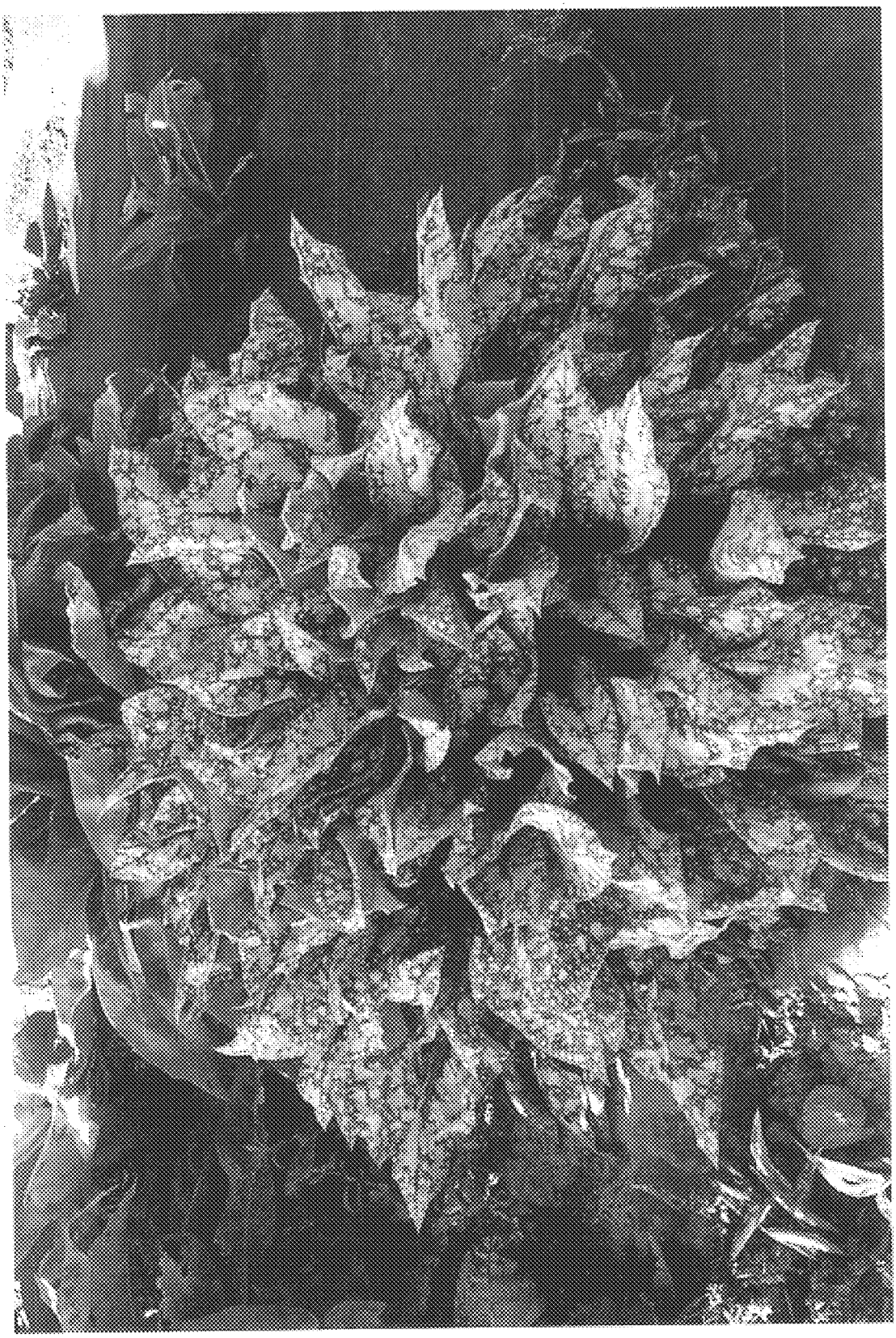

* * * * *